United States Patent [19]
Whiteside

[11] Patent Number: 5,755,805
[45] Date of Patent: May 26, 1998

[54] TAPERED PROSTHESIS COMPONENT

[76] Inventor: Leo A. Whiteside, 14825 Sugarwood Trail, Chesterfield, Mo. 63017

[21] Appl. No.: 686,978

[22] Filed: Jul. 25, 1996

[51] Int. Cl.$^6$ .................................... A61F 2/30; A61F 2/32
[52] U.S. Cl. ............................................. 623/22; 623/18
[58] Field of Search ............................. 623/23, 18, 22; 606/62, 67

[56] References Cited

U.S. PATENT DOCUMENTS

| | | | |
|---|---|---|---|
| 4,944,761 | 7/1990 | Stuhmer et al. | 623/23 |
| 5,169,401 | 12/1992 | Lester et al. | 606/79 |

*Primary Examiner*—John G. Weiss
*Assistant Examiner*—John M. Back
*Attorney, Agent, or Firm*—Polster, Lieder, Woodruff & Lucchesi, L.C.

[57] ABSTRACT

A prosthesis component for implantation into a bone canal has a tapered diaphyseal segment with one or more ridges, the ridges arranged coaxially from the distal to the proximal end of the diaphyseal segment of the component. Each ridge has a sharp longitudinal edge and at least one transverse sharp leading edge which forms a step that cuts into bone adjacent to the bone canal during implantation. The amount of taper of the outer dimensions of the ridges is controlled by the number and size of the steps and corresponds to an amount of taper of a bone canal into which the component is to be implanted. The outer edges of the ridges are parallel to the central longitudinal axis of the prosthesis component or divergent from this axis no more than 3° from distal to proximal. In one embodiment the cross-sectional shape of the component is generally rectangular and in another, the cross-sectional shape is generally cylindrical. A method is described for inserting the tapered prosthesis whereby the central medullary canal of the diaphyseal portion of the bone is broached such that the sharp edges of the steps cut a groove in the surfaces of the bone and thus engage the dense bone of the inner surface of the diaphyseal medullary canal to resist torsional loads applied to the prosthesis.

13 Claims, 6 Drawing Sheets

TAPERED PROSTHESIS COMPONENT

BACKGROUND OF THE INVENTION

Replacing worn or arthritic joints with biocompatible materials is a common surgical operation in human and animal medicine. Attachment of these artificial components to bone is a complex mechanical task. Typically one side of the joint requires fixation of an anchoring stem in the center of one end of a long bone. In the hip, the ball portion of the joint is attached to the upper end of the femur by means of a femoral component that transverses the metaphysis and engages the diaphysis. These femoral components are comprised of a diaphyseal segment which typically consists of a straight or tapered stem with an oval or round cross-sectional shape which is driven into a prepared femoral medullary canal. Preparation of the medullary canal involves reaming or broaching the canal into a similar shape. The metaphyseal segment, which is either integral with or modularly connected to the diaphyseal segment, is designed for implantation into the upper extremity of a femur, including the neck. These femoral components can be affixed to the femur with acrylic bone cement, or they can be press-fit into the femur and fixed initially by friction and later by bone ingrowth or attachment to the femoral component.

The chief complication of the femoral components that are press-fit is loosening before they can be permanently affixed to bone by ingrowth or attachment of bone. Torsional forces are the chief cause of loosening of the femoral component, and all femoral components have some aspect of their configuration designed to resist torsional force. The component sold under the trade designation Replica by DePuy, which is well known in the art, has a diaphyseal segment, or distal stem, comprised of a cylindrical stem with a plurality of grooves and ridges extending between the proximal and distal ends. The overall size of the stem, including the grooves, is slightly larger than the prepared medullary canal into which the stem is to be implanted. The ridges are utilized to provide tight distal fixation of the stem so as to prevent the stem from loosening as a result of torsional loads. However, because of the position of these ridges at the distal end of the diaphyseal segment of the component, the rotational position of the femoral component is set long before the component nears its final seating position, thereby preventing precise adjustment of the metaphyseal segment's rotational position. Also, because the diaphyseal segment is not tapered, the medullary canal must be reamed to accept the component, and this may cause damage to the bone.

Another type of femoral component is that sold under the trade designation Anatomic Medullary Locking (AML) stem by DePuy. Its distal stem has a porous coating on its distal portion which creates small grooves in the reamed inner surface of the diaphyseal bone as the implant is driven into the bone. This stem has the same disadvantages as those of the cylindrical femoral components with grooves and ridges in achieving correct rotational position of the metaphyseal segment; that is, they become locked in rotational position long before they are fully inserted and seated into the metaphyseal cavity. Also, the medullary canal of the bone must be reamed to accept the component. A further disadvantage is that the growth of the bone into porous coating of the femur which in turn has the long term effect of causing loss of bone.

Another femoral component of the prior art is made by Link. This femoral component has a plurality of ridges extending longitudinally along its surface. These ridges are interrupted by notches that meet to form a saw tooth pattern. The saw tooth pattern is restricted to the upper portion of the stem, and does not engage the hard cortical bone of the diaphysis. The teeth cut grooves in the cancellous bone of the upper femoral metaphysis, and these grooves accommodate the ridges of the femoral component. The saw tooth edges of the ridges improve fixation and help prevent fracture of the femur, but after bone healing has occurred, they become encased in bone, making extraction difficult in the event that a revision is necessary. These ridges and teeth are located in the metaphyseal portion of the bone, and are not designed to cut grooves or to lock into the diaphyseal cortical bone.

Another femoral component of the prior art is that sold under the trade designation S-Rom by Joint Medical Products. This component overcomes the problem of obtaining a precise rotational position by providing a modular connection between the distal stem and the metaphyseal segment. The distal stem also is provided with a plurality of ridges, and has a large slot in its distal end which gives the distal stem an overall appearance similar to that of a clothespin. As the distal stem is driven into a medullary canal, the distal slot closes to help prevent fracture. A proximal end of the medullary canal with the distal stem then is inserted through this sleeve. The distal stem also has a tapered surface on its proximal end which is complementary to the taper of the proximal sleeve, so that the distal stem has been driven into the medullary canal, the modular metaphyseal sleeve is inserted first and correctly positioned in the prepared proximal femur. The modular diaphyseal segment is then inserted through the modular metaphyseal sleeve to finally fit tightly in the diaphyseal portion of the femur. The disadvantages of this femoral component are that it is expensive to manufacture, difficult to insert, and it relies on a taper junction to support the entire body weight. This taper junction is known to wear, to fret and to allow fluid to leak through. Also, the diaphyseal component is cylindrical, so the medullary canal must be reamed to a cylindrical shape to accept the implant.

Another modular femoral component is that sold under the trade designation Impact Stem by Biomet, Inc. This component functions similarly to the S-Rom stem but the taper junction on the proximal end of the distal stem is such that the diameter of the bunion taper decreases in the proximal direction. As a result, the proximal sleeve of the S-Rom stem is eliminated. The distal stem is inserted into the medullary canal, and then the modular proximal segment (metaphyseal segment) is impacted onto the taper portion of the distal stem within the proximal end of a femur. Also, the distal segment is cylindrical, so that the diaphyseal medullary canal must be reamed to accept the implant.

Another femoral component of the prior art is that sold under the trade designation Omnifit by Osteonics. This femoral component has longitudinal ridges on the anterior and posterior portions of the metaphyseal end of the leading edges which are designed to capture cancellous bone or cement and to transfer axial load more efficiently. They do not impart a tapered shape to the outer dimensions of the implant, nor do they engage the cortical inner surface of the diaphyseal portion of the bone. The distal segment of this diaphyseal component is tapered and smooth, and does not have ridges.

Another implant of the prior art is the S-Rom total knee replacement rotating hinge sold by Johnson and Johnson. The metaphyseal sections of the femoral and tibial components have a tapered shape that is achieved by successive ridges, and the cross-sectional shape is polygonal so that the sides form edges. The purpose of this configuration is to apply compressive load to the cancellous bone in the metaphysis. The diaphyseal portions of both the femoral and tibial components are non-tapered and have longitudinal ridges, but do not have steps on the ridges.

Many of the distal stems of the prior art are cylindrical and non-tapered. Because a typical femoral medullary canal is tapered, the medullary canal must be reamed to a cylindrical shape prior to insertion of these distal stems, which requires removal of hard cortical bone. Such cylindrical reaming is difficult to perform, and often results in damage to the femur. Moreover, this reaming of the femur also renders the femur more susceptible to fracture by distal stems which must be impacted into the medullary canal.

Some of the distal stems of the prior art are tapered, so that less bone is removed in preparing the canal of the femur. These tapered stems have several disadvantages. If the tapered stem is seated in hard bone it easily can wedge the femur apart and cause it to fracture. If the tapered distal portion of the implant does seat on the inner walls of the femoral diaphysis and the bone does not break, then the distal portion of the stem becomes the main weight-bearing surface, and the proximal portion of the femur receives less load, and thus bone loss occurs due to stress relief atrophy. If the tapered distal segment does not seat against the inner diaphyseal walls, then this portion of the implant cannot contribute to torsional fixation so that the implant is then dependent on only the proximal metaphyseal femoral bone for torsional fixation, and thus in this situation torsional fixation is inadequate.

It would be advantageous to have a mechanism that would allow the femoral implant to be inserted in the femur and to achieve rigid fixation against torsional loads by mechanically locking to the inner surface of the diaphyseal and metaphyseal bone without compromising rotational positioning of the femoral implant, removing excessive bone, inordinately risking fracture of the bone, compromising extractability, or relying on modularity to achieve these goals. Also the distal fixation mechanism should not depend on porous coating for its immediate effect, since a long-term effect of porous coating in the distal portion of the femoral implant can be loss of bone in the upper femur. The invention described here accomplishes those goals with a simple mechanism that makes the operation easier to do than the methods now available. It is also less expensive to manufacture.

SUMMARY OF THE INVENTION

It is among the principal objects of the present invention to provide a prosthesis with tapered diaphyseal segment that resists torsional forces when inserted into bone.

It is another object of the present invention to provide such a tapered prosthesis that mechanically locks to the inner surfaces of the bone so as to resist torsional forces.

Still another object of the present invention is to provide such a prosthesis with tapered diaphyseal segment that does not promote weakness or fracture of the bone upon insertion or after insertion.

Yet another object of the present invention is to provide such a prosthesis that conforms to the taper of the diaphyseal portion of the bone so as to prevent fracture of the bone upon insertion.

Another object of the invention is to provide such a tapered prosthesis that is economical to manufacture, relatively easy to use, simplifies the surgical implantation process and is well suited for its intended purposes.

In accordance with the invention, generally stated, a prosthesis with tapered diaphyseal segment is provided having at least two longitudinal ridges with at least one step with a sharp leading edge facing distally to act as a cutting edge and thus to groove the inner surface of the diaphyseal cortical bone. In the preferred embodiment for human total hip replacement, the tapered prosthesis component is a diaphyseal segment, or distal stem, of a femoral component for a hip replacement system. The distal stem has a plurality of sides that meet to form longitudinal parallel ridges coaxially aligned along the entire extent of the diaphyseal section of the femoral implant. Each ridge has at least one step with a transverse leading edge. The leading edge and the corners join to form a sharp angular configuration. The outer dimensions of the ridges decrease in stepwise manner from the most proximal to the most distal end. As a result, the distal stem has a tapered configuration which corresponds to the tapered configuration of a femoral medullary canal into which the distal stem is designed for insertion. For this reason, the need for cylindrical reaming of the femoral medullary canal prior to insertion of the distal stem is eliminated in most cases, and a broaching or conical reaming procedure can be used instead.

The steps, leading edges, and sharp corners of the ridges have angular configurations to cut into the bone adjacent to the femoral medullary canal as the distal stem of the femoral component is impacted. Hence, the distal stem cuts into the bone as opposed to wedging the bone apart, and in this manner, reduces the likelihood of fracturing the femur into which the femoral component is implanted. Moreover, by cutting into the bone adjacent to the medullary canal, an interlocking effect is achieved at several locations between the distal stem and the femur.

The distal stem is provided with a rounded tip on its distal end, which helps to avoid distal impingement between the femoral component and the femur. Since the ridges are axially aligned or parallel to one another or diverge slightly from distal to proximal, healing of bone closely around the surface of the component does not interfere with removal of the component.

To implant the tapered prosthesis component of the preferred embodiment, a length and an amount of taper must first be determined for a femoral medullary canal into which the distal segment is to be implanted. Thereafter, a distal segment can be chosen which has a configuration that is complementary to the predetermined configurations of the medullary canal. Various configurations of the distal stem are achieved by varying the dimensions of the outer surface of the ridges or by varying the number or size of the steps interrupting the ridges, or by doing both. Once the distal stem has been chosen and the medullary canal broached, the femoral component can be inserted. As a result of the overall tapered configuration of the distal segment of the femoral component, the proximal segment of the femoral component can be brought close to its final seating position prior to final impaction of the distal segment of the femoral component. After insertion, the femoral component is supported only by the leading edges of the steps which are beginning to engage the inner surfaces of the diaphyseal medullary canal. However, the femoral component is not yet impacted into final position. This allows for precise rotational adjustment of the femoral component just prior to impaction, thereby eliminating the need for modular femoral components. After insertion and adjustment of the rotational position, the femoral component is impacted to drive the distal stem further into the medullary canal and into its final seating position.

In a second preferred embodiment, the tapered prosthesis component is a diaphyseal segment, or distal stem, of a femoral component for a hip replacement system. The distal stem has a plurality of ridges on its outer surface. Each ridge is interrupted by at least one step with a transverse orientation and sharp leading edge. The cross-sectional area of the distal stem decreases from proximal to distal and the circumference defined by the outer surfaces of the ridges decreases in a step-wise fashion with each step and leading edge. As a result, the distal stem has a tapered configuration which corresponds to the tapered configuration of a femoral medullary canal into which the distal stem is designed for insertion.

Each leading edge has an angular configuration. As a result of this configuration, the leading edges of the ridges are sharp and cut into the bone adjacent to the femoral medullary canal as the distal stem of the femoral component is impacted.

While principal advantages and features of the invention have been described above, a greater understanding of the invention may be attained by referring to the drawings and the description of the preferred embodiment which follow.

BRIEF DESCRIPTION OF THE DRAWINGS

Corresponding reference figures denote corresponding elements throughout the description of the preferred embodiments.

DETAILED DESCRIPTION OF THE PREFERRED EMBODIMENT

Figures 1, 2, 2A:
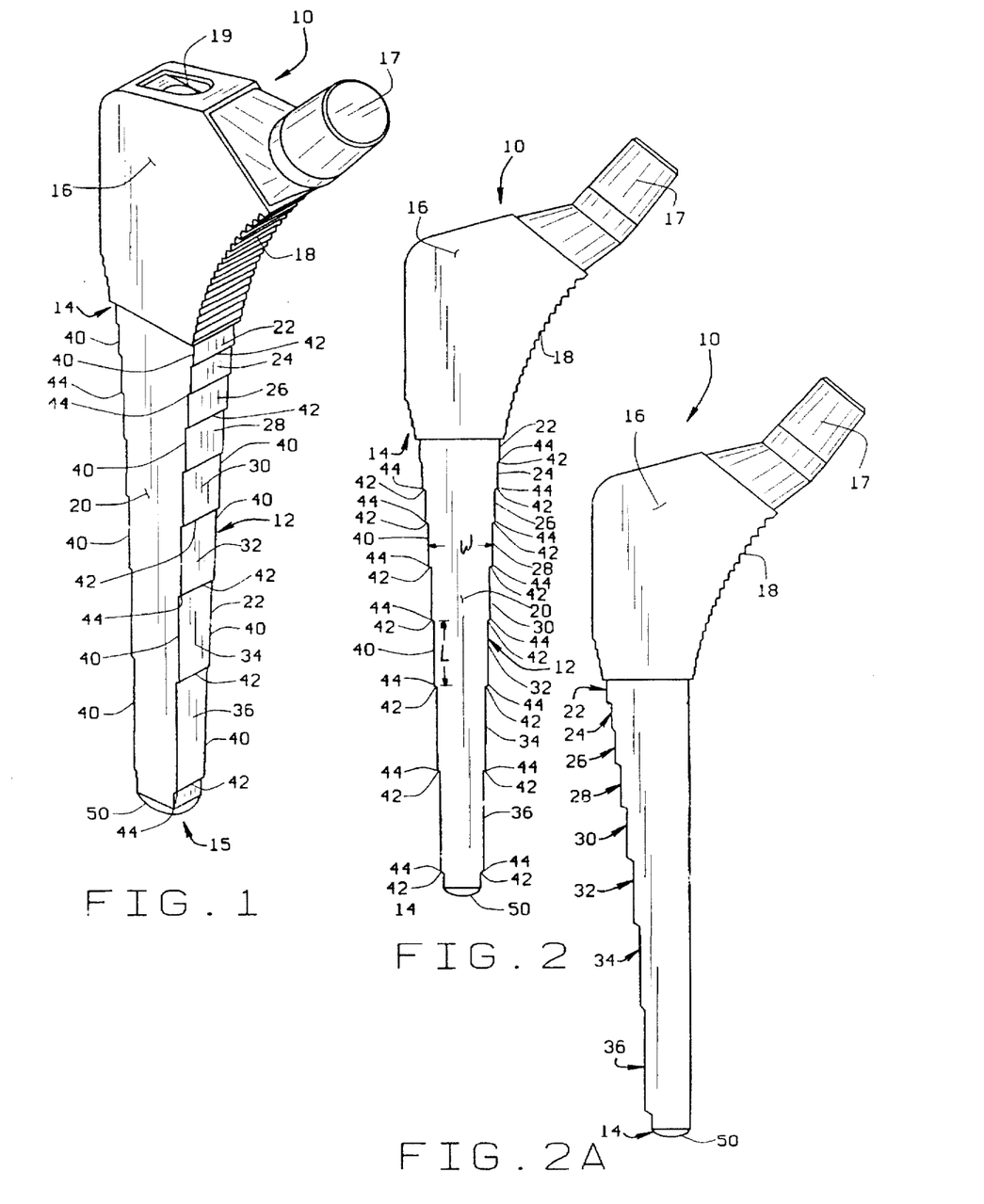
FIG. 1 is a perspective view of a prosthesis component according to the present invention.
FIG. 2 is a side elevational view of the prosthesis component of FIG. 1.
FIG. 2A is a side elevational view of a prosthesis component according to the present invention employing a diaphyseal taper only on one side.

Together with an acetabular component (not shown), the femoral component 10 comprises the key components of a joint replacement system. The femoral head implant and the acetabular component are designed to replicate the articulation between the head of the femur and the acetabulum of an os innominatum, or pelvic girdle. As shown in FIG. 1, a tapered prosthesis component of the preferred embodiment is a diaphyseal segment of a femoral component 10 for a hip replacement system. The diaphyseal segment, or distal stem 12, has a proximal end 14 and a distal end 15. A metaphyseal segment 16, located above the proximal end 14, is configured for implantation into the upper extremity of a femur F (FIGS. 3 and 4), and is joined with a femoral head implant 17. Metaphyseal section 16 has a curved face section comprised of a plurality of sharp, horizontally extending ridges 18. There is also a depression 19 formed in the top surface of the metaphyseal section configured to accept a driving tool to seat the femoral component in the medullary canal, as explained below. Although the distal stem 12 is shown as being an integral part of the femoral component, the distal stem 12 can also be part of modular femoral components that are well known in the art or can be employed in the replacement of other joints such as the knee, shoulder, ankle metacarpal and so on.

The distal stem 12 of the illustrated embodiment includes a pair of uniform side walls 20 and 22 and a plurality of sequentially stepped front and rear rectangular faces 22, 24, 26, 28, 30, 32, 34 and 36. The walls 20 and 22 and the front and rear rectangular faces give each section a rectangular peripheral shape. The edges of these walls meet to form corners or ridges, and the ridges are interrupted by steps that have sharp leading edges.

As can be seen in FIGS. 1 and 2, the distal segment of the femoral stem tapers from the proximal end 14 to the distal end 15. It will be appreciated that in the preferred embodiment of FIGS. 1–4, the taper is achieved by decreasing the horizontal width W at each point where a step exists from the proximal to the distal end. As a result, the distal stem 12 has a downwardly tapered configuration. It also will be appreciated that the length L between the steps increases from the proximal to the distal end of the distal stem. More closely spaced steps such as those separating surfaces 22–28 are required near the proximal end to accommodate a greater angle of taper within the upper end of the medullary canal. However, the amount of taper of the distal stem can be adjusted as needed for a particular application, as described below.

Figure 3:
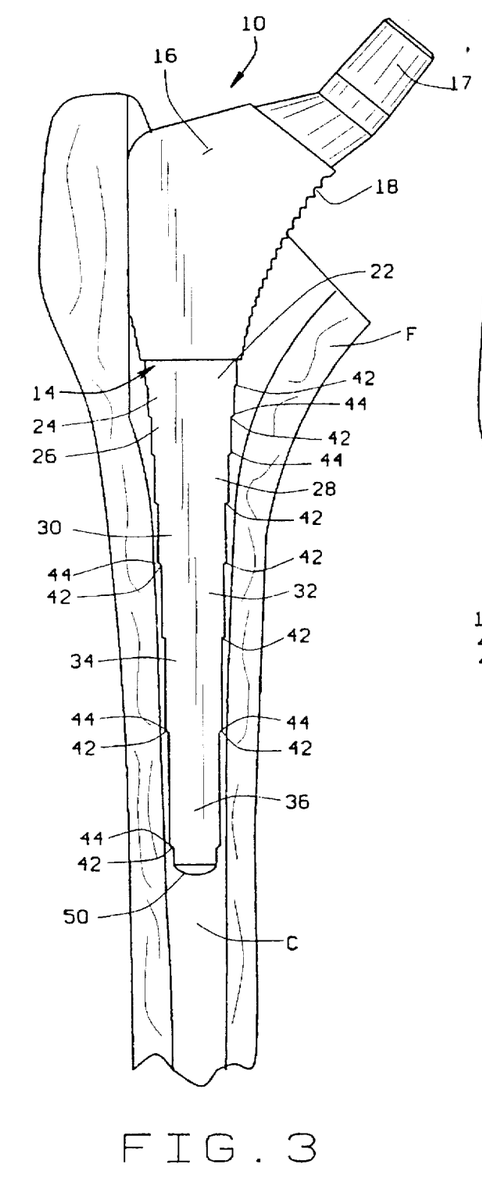
FIG. 3 is a cut away view of a femur with the prosthesis component of FIG. 1 inserted therein.
Figure 4:
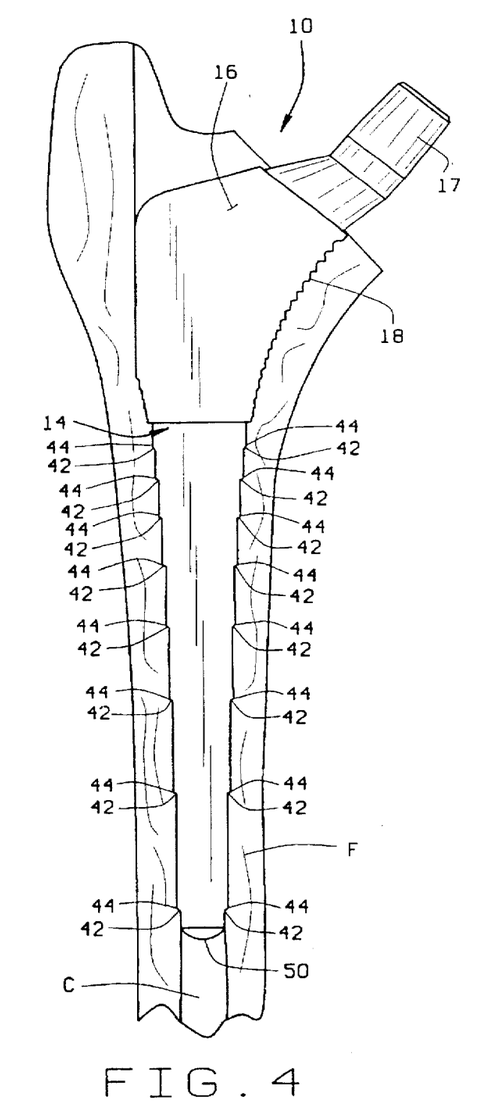
FIG. 4 is a cut away of the femur of FIG. 3 after the prosthesis component has been impacted into a final seating position.

Due to the tapered configuration of the distal stem 12, the need for cylindrical reaming of the femoral medullary canal is eliminated, and the metaphyseal segment can be brought close to its final seating position, shown in FIGS. 3 and 4, prior to driving the distal stem into the femoral medullary canal during the implantation process.

The cross-section of the distal stem of the preferred embodiment has a substantially rectangular peripheral shape. It will be appreciated that although in the illustrated embodiment the cross section has a rectangular peripheral shape, the invention encompasses any tetrahedron or, if the distal stem contains the requisite sharp edges, a triangle or other appropriate geometric cross-sectional shape. Other embodiments could include peripheral shapes that are circular, as will be used to form a solid shape.

Figure 7:
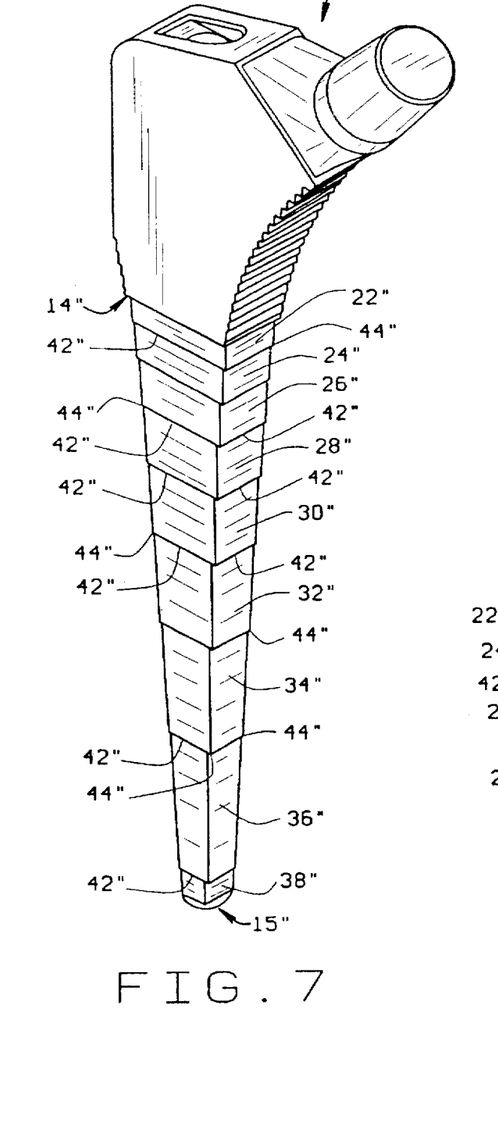
FIG. 7 is a perspective view of another embodiment of a prosthesis component according to the present invention.
Figure 8:
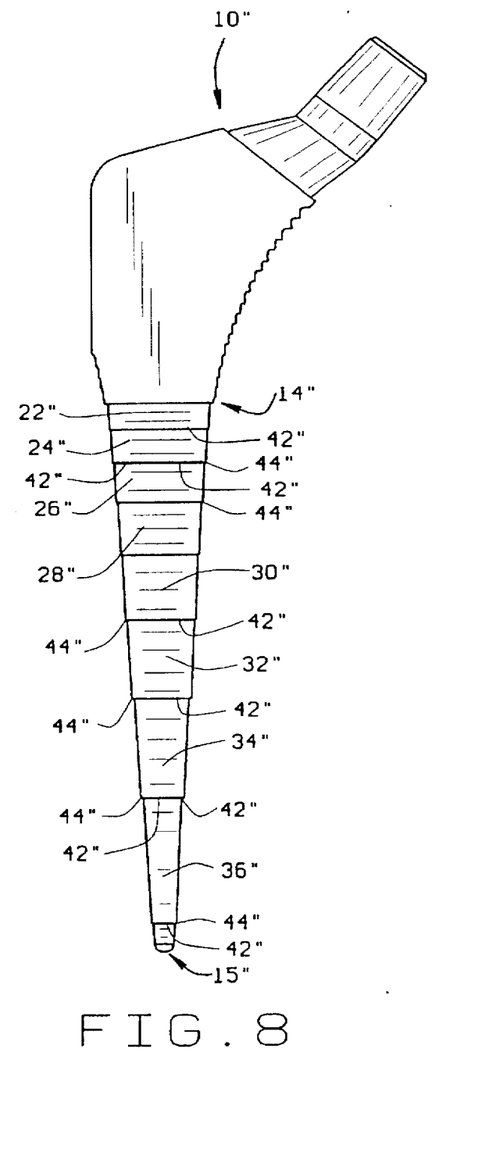
FIG. 8 is a side elevational view of the prosthesis component of FIG. 7.

The distal stem 12 of the preferred embodiment, therefore, has the longitudinal ridges arranged coaxially between the proximal end 14 and the distal end 15. However, for a specific application, it may be necessary to arrange the longitudinal ridges in a noncoaxial manner. For example, viewing the distal stem in FIG. 2A, it may be necessary for the faces on the right side of the distal section 12 to be co-planar, so that the overall configuration of the distal stem is tapered only on the left side. Obviously, this arrangement can be reversed and the distal stem be tapered on the right side and substantially straight on the left side, if required by the specific application. Such configurations of the distal stem 12 may be required for a femoral medullary canal having an irregular shape so that unnecessary reaming of the medullary canal can be avoided. Further, as will be described below with reference to other embodiments, the configuration of the distal stem may be so arranged such that none of the sides are co-planer (FIGS. 5 and 6) or one or more faces of each individual section may have a taper no greater than 3° (FIGS. 7 and 8).

Figures 5, 6:
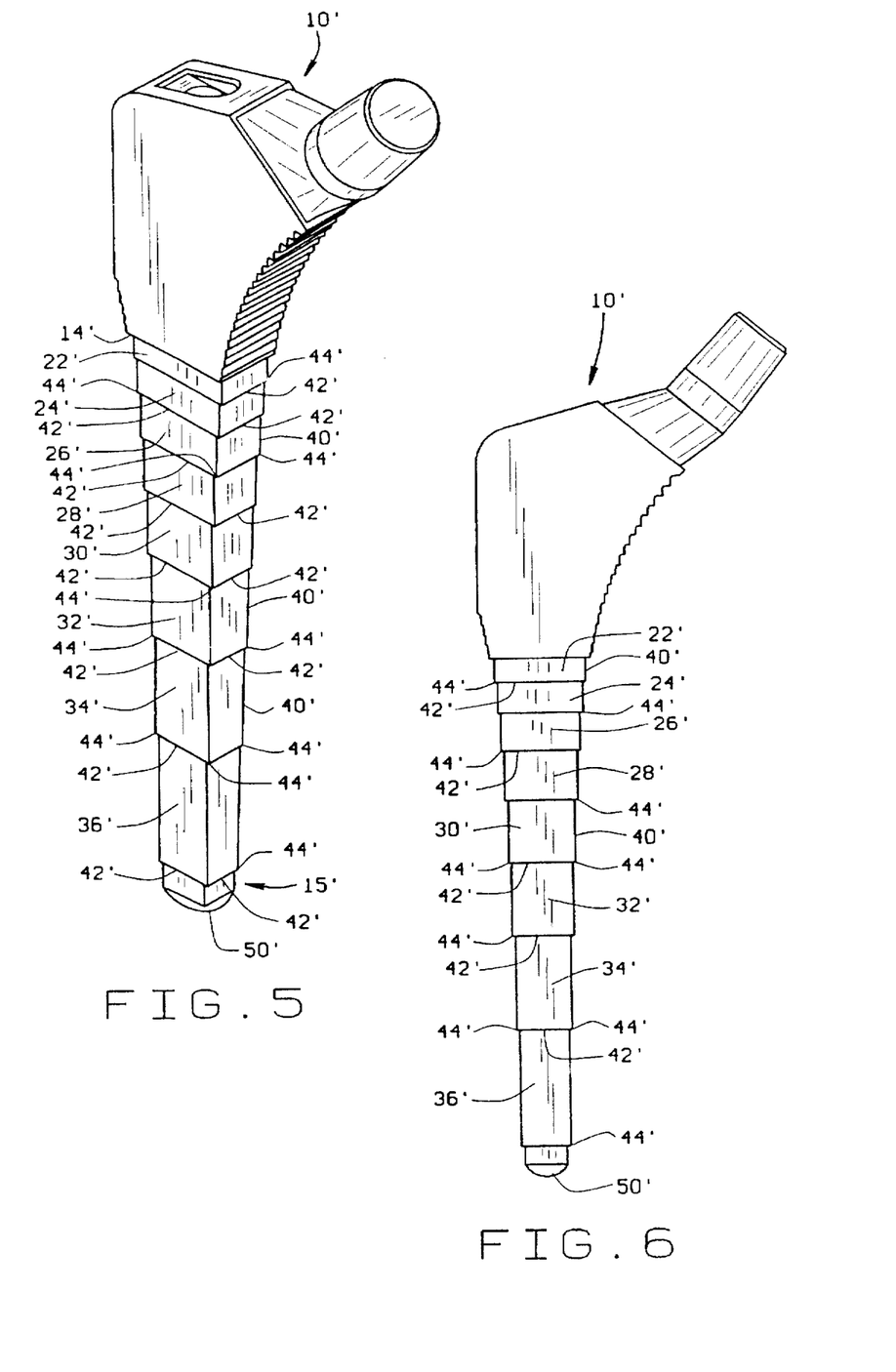
FIG. 5 is a perspective view of another embodiment of a prosthesis component according to the present invention.
FIG. 6 is a side elevational view of the prosthesis component of FIG. 1.

Returning now to the detailed description of the embodiment of FIGS. 1–4, the distal stem is provided with four sharp corners or ridges, as indicated in each portion of the distal stem by reference numeral 40. Each ridge also has a relatively sharp distal or leading edge 42 which abuts the sharp ridges 40 to form sharp cutting steps 44 at the juncture of the leading edges and the sharp ridges. Although the leading edges to the steps are shown having a sharp right angle configuration, the leading edges may have a more acute angular configuration. The ridges 40 are utilized to provide a high degree of rotational stability, including immediate intraoperative stability, for the distal stem 12 upon implantation into a femoral medullary canal C. The ridges 40 and steps 44 are colinearly aligned with those above and below. In another embodiment of this invention, as shown in FIGS. 5 and 6, which will be described in greater detail below, the ridges 40' and their steps 44' are aligned but staggered so that the step 44' prepares a groove in the bone for its ridge 40', but does not participate in preparing the way for more proximal points 44' and corners 40'.

In the distal stem of the embodiment illustrated in FIGS. 1–4, the ridges are formed by two flat surfaces (i.e. side walls 20 and 22 and the two stepped surfaces) arranged at a right (90°) angle to one another as shown in FIG. 2. However, other types of ridge configurations can be utilized, such as flutes, while maintaining the desirable attributes of the ridge of the preferred embodiment. The ridges 40 could be rounded and still perform the function of the ridge as long as an angular point 44 was present at the distal extreme of the ridges to provide the ability to cut a groove in the inner surface of the bone and to allow the ridge to fit tightly into the groove.

As can be appreciated from FIGS. 3 and 4, since each ridge 40 having a step 44 has an angular or sharp configuration that cuts into the tapered surface of the femoral medullary canal, the distal stem 12 does not wedge the femur F apart, which can result in fracture. By cutting into the femur, the ridge 40 helps to provide an interlocking effect between the distal stem and the femur that is more extensive than that obtained by prior art distal stems. Although the angular configurations of the ridges are shown as right angles in FIGS. 1, 3, and 4, more or less acute angular configurations can be utilized with similar effects.

Although the distal stem is shown in FIGS. 1–4 as having parallel sides, it is possible for the sides to be tapered to some degree, provided that the distal stem tapers from proximal to distal, as will be explained below relative to FIGS. 7 and 8.

As shown in FIG. 1, the distal stem 12 also is provided with a rounded tip 50 on the distal end. The rounded tip 50 helps to avoid distal impingement between the distal stem and the femur during implantation of the femoral component.

To implant the distal stem 12 of the preferred embodiment, one must first determine a length and an amount of taper of a femoral medullary canal C into which the distal stem is to be implanted. Anterior-posterior and lateral radiographs can be utilized to make this determination. Thereafter a femoral component can be selected with distal stem 12 having the same length and an amount of taper as the medullary canal C. The amount of taper of the distal stem 12 of the femoral component varies with the length L between the steps by varying the number of steps, and with the size of the steps. Typically, the number of steps utilized will be larger for medullary canals having greater than normal amount of taper.

Next, the femoral head (not shown) is resected to expose the medullary canal C. If necessary, the medullary canal C can be prepared with a broach, or reamer, prior to insertion of the femoral component. As shown in FIG. 3, the femoral component 10 is then inserted, distal end 15 first, into the exposed medullary canal C. Due to the taper of the distal stem 12, the section closest to the proximal end is brought close to its final seating position before impacting, thereby allowing precise adjustment of rotational position just prior to impaction. The femoral component 10 can then be impacted with an appropriate tool positioned in depression 19 of the metaphyseal section, causing the sharp steps 44, the ridges 40 and the leading edges 42 to cut into the bone adjacent to the medullary canal to drive the femoral component several millimeters further into the medullary canal without wedging apart the femur and thus allowing tight fixation without risking fracture of the femur.

While the tapered prosthesis component 10 of the present invention has been described as a femoral component for a hip replacement system, this description is not intended to be limiting. As stated above, the tapered prosthesis component 10 of the present invention can be utilized in other articulating anatomical joint systems, such as shoulder joint systems, and is equally suited for other types of uses, including veterinary applications.

FIGS. 5 and 6 illustrate another preferred embodiment of the prosthesis component of the present invention, indicated generally by reference numeral 10'. Prosthesis component 10' has a distal stem 12', having a proximal end 14' and a distal end 15', which is comprised of a plurality of surfaces 22', 24', 26', 28', 30', 32', 34' and 36'. The surfaces meet to form parallel longitudinal ridges. In this configuration sides and ridges are interrupted with steps so that the distal stem tapers in a stepwise manner from proximal to distal. The four faces between the steps intersect at a 90° angle forming four sharp corners or ridges 40' and four sharp leading edges 42' which combine to form four steps interrupting the four ridges. It will appreciated that, in contrast to the embodiment illustrated in FIGS. 1–4, the embodiment of FIGS. 5 and 6 has two additional steps 42' on each side.

FIGS. 7 and 8 illustrate yet another embodiment of the tapered prosthesis component indicated generally by reference numeral 10". Component 10" has a distal stem 12" with a proximal end 14" and a distal end 15". Distal stem 12" has a plurality of coaxially aligned surfaces 22", 24", 26", 28", 30" 32", 34' and 38". It will be noted that each respective surface has four faces or walls that angle downwardly and inwardly. The taper is preferably 3° or less. As with the previous embodiment, the surfaces abut and define sharp corners or ridges 40". Each surface also has a step with sharp leading edge 42". The ridges and leading edges join to form four sharp steps 44". It will be noted that as a result of this novel configuration, the ridges 40" and steps 44" of succeeding tapered sections are staggered and are not in alignment with the preceding ridges and steps. As the prosthesis is impacted into the medullary canal, each ridge 44" and step 44" makes its own track in the femur and effectively locks the prosthesis in place.

FIGS. 9–12 illustrate another embodiment of the tapered prosthesis component, indicated generally by reference number 50. Prosthesis component 50 has a diaphyseal segment or distal stem 52. Distal stem 52 has a proximal end 54 and a distal end 56. Attached to the proximal end 52 is a metaphyseal segment 58 that is configured for implantation into the upper extremity of a femur and is joined with a femoral head implant 60.

The distal stem 52 includes a plurality of longitudinal ridges 62, 64, 66, and 68. As can be see in FIGS. 9 and 10, the cross-sectional areas of the distal stem 62, 64, 66 and 68 decreases from the proximal to the distal end due to steps in the ridges. As a result, the distal stem 52 has a tapered configuration. However, the amount of taper can be varied for a particular application.

Figure 10:
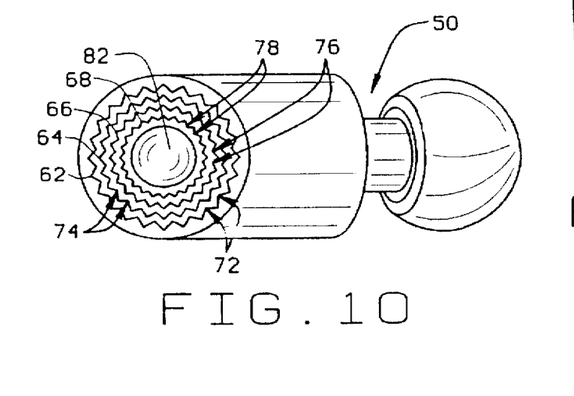
FIG. 10 is a partial distal end view of the tapered prosthesis component of FIG. 9.
Figure 11:
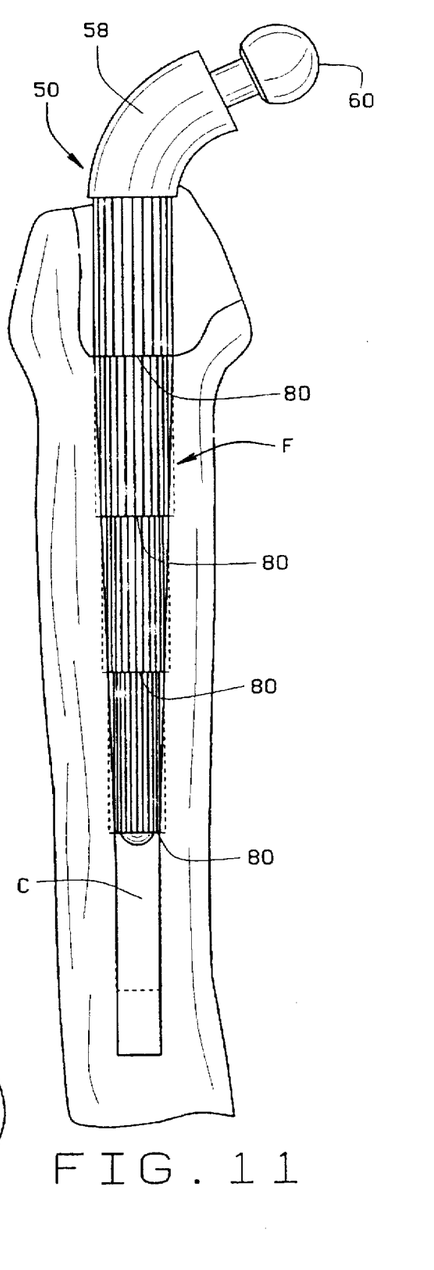
FIG. 11 is a cut away view of a femur with a the prosthesis component of FIG. 9 inserted therein.
Figure 12:
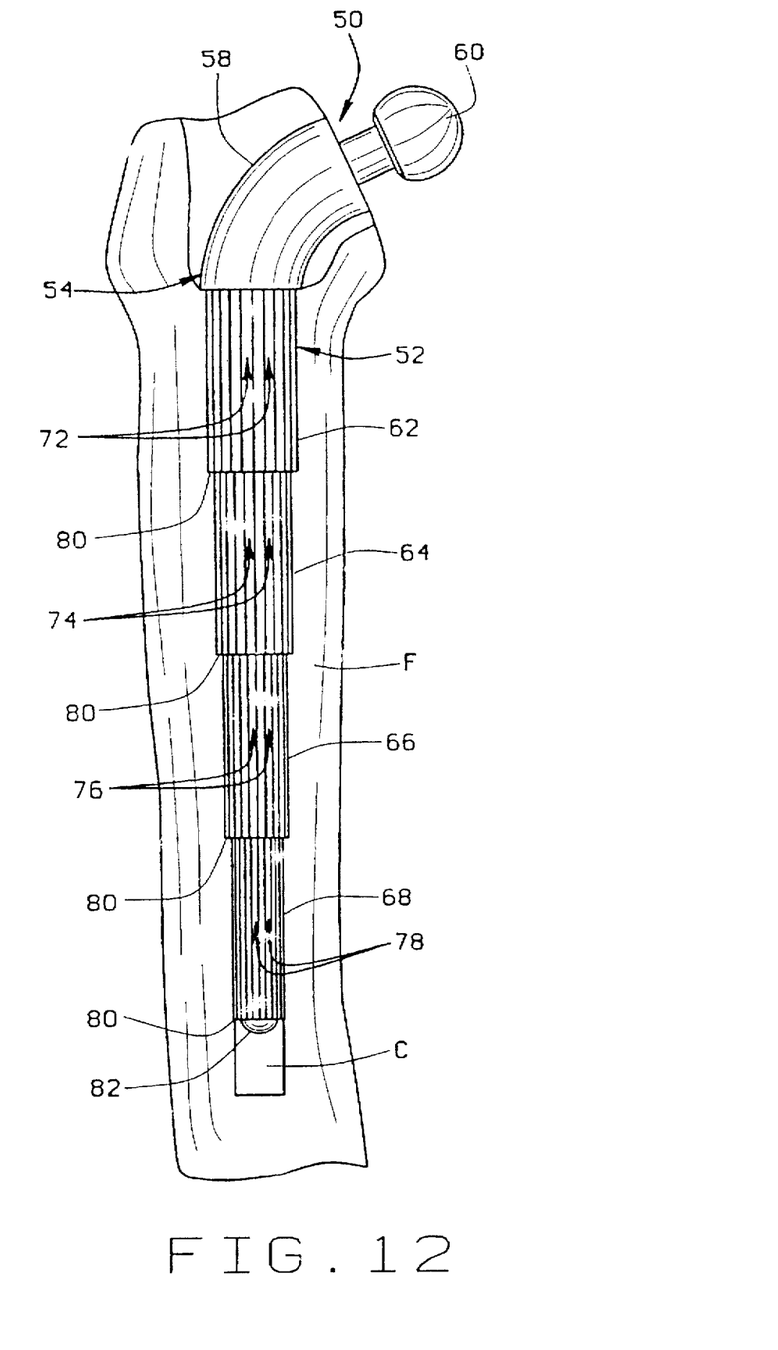
FIG. 12 is a cut away view of the femur of FIG. 11 after the prosthesis component has been impacted into a final seating position.

As shown in FIG. 10, the distal stem has a tapered circular peripheral shape. Although the peripheral shape of the distal stem is shown as being circular, "cylindrical" is intended to include peripheral shapes that are ellipsoidal, or any other types of closed curves which are included within the ordinary meaning of this term.

The distal stem 52 has the ridges 62, 64, 66 and 68 arranged coaxially between the proximal end 54 and the distal end 56. However, for a specific application, it may be necessary to arrange the ridges in a non-coaxial manner. For example, viewing the distal stem 52 in FIG. 9, it may be necessary for the right sides of the ridges to be coextensive, so that the distal stem 52 is tapered only on the left side. Additionally, while the peripheral shapes of the circumference of the outer surface of the ridges have been described as being substantially identical, the peripheral shape of one position of the distal stem can be different from the peripheral shape of another portion, if necessary. Although the embodiment illustrated has four steps, each being a transverse line around the distal stem, it will be appreciated that the steps need not be arranged evenly in transverse planes, but could be staggered or randomly arranged.

The number of steps will vary according to the length of the femoral medullary canal into which the distal stem 52 is to be implanted. For example more than four and as few as one step for each ridge may be used. Moreover, increasing the number of steps will increase the taper of the distal stem 52.

Figure 9:
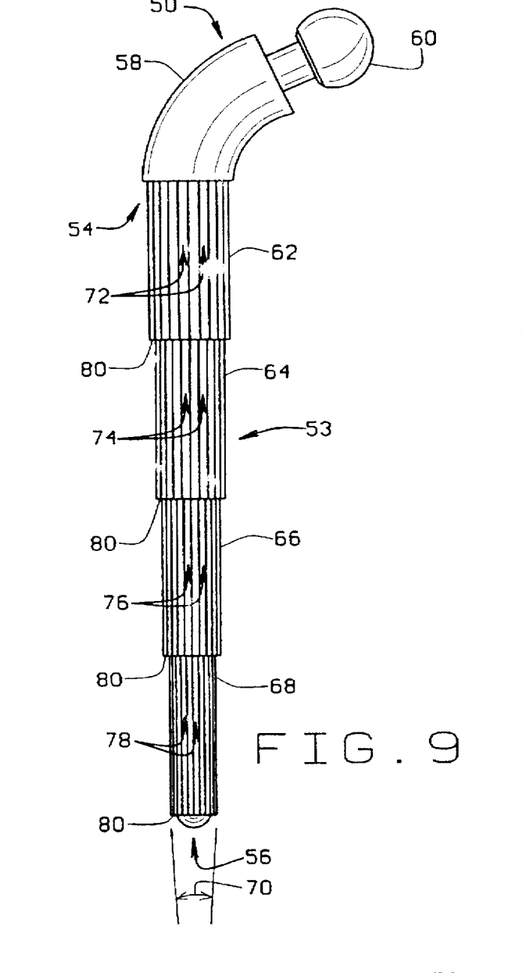
FIG. 9 is a perspective view of another embodiment of a tapered prosthesis component according to the present invention.

The distal segment is provided with a plurality of ridges 72, 74, 76 and 78, respectively. These ridges are utilized to provide a high degree of rotational stability, including immediate intraoperative stability upon implantation in the femoral medullary canal C, as do the ridges that are formed by the sharp corners of the embodiments previously described. As shown in FIG. 9, the ridges extend between the proximal end 54 and the distal end 56 of the distal stem. Moreover, as best seen in FIG. 10, the ridges 72, 74, 76 and 78 are provided in axial alignment. In other words, the ridges of one cylindrical section would be coextensive with the ridges of an adjacent cylindrical section but for the difference in the diameters of the stem as described by the other surface of the ridges above and below each step (measured between the valleys of the grooves) and the difference in size of the ridges of the respective cylindrical sections.

In the distal stem 52, the plurality of ridges 72, 74, 76 and 78 have a triangular configuration, as shown in FIG. 10. However, other types of ridge configurations can be utilized, such as flutes, while maintaining the desirable attributes of the ridges of the preferred embodiment.

Each leading edge 80 has an angular configuration so that the leading edge 80 of each cylindrical section cuts into bone F adjacent to the femoral medullary canal C upon insertion and impaction of the distal stem 52, thereby preparing the way for the plurality of ridges 72, 74, 76 and 78. Because the leading edges 80 have a sharp angular configuration that cuts into the tapered surface of the femoral medullary canal C, the distal stem 52 does not wedge the femur F apart, which could result in fracture. By cutting into the femur F, the leading edges 80 help to provide an interlocking effect between the distal stem 52 and the femur F that is more extensive that obtained by distal stems of the prior art. Although the angular configurations of the leading edges 80 are shown as right angles in FIGS. 9, 10 and 11, more acute angular configurations can be utilized with similar effect. Although the ridges are shown in the figures to be parallel, it is possible for the ridges to converge to some degree, analogous to the embodiment illustrated in FIGS. 7 and 8.

As shown in FIG. 10, the distal stem 52 also is provided with a rounded tip 82 on the distal end 56. The rounded tip helps to avoid distal impingement between the distal stem 52 and the femur F after implantation.

It will be appreciated that the above described alternative embodiments of the prosthesis component of the present inventions are implanted in the femoral medullary canal C in the same manner as previously described relative to the first preferred embodiment.

There are various changes and modifications which may be made to the invention as would be apparent to those skilled in the art. Although the overall cross-sectional shape of the femoral component is depicted in FIGS. 1–8 as rectangular and FIGS. 10–13 as cylindrical, other cross-sectional shapes such as spline-shaped, hexagonal and triangular could be combined to form ridges interrupted with steps. However, these changes or modifications are included in the teaching of the disclosure, and it is intended that the invention be limited only by the scope of the claims appended hereto.

I claim:

1. A prosthesis component for implantation into a bone canal comprising a diaphyseal portion of the component including axially opposite first and second ends and at least two bone cutting ridges longitudinally arranged between the first and second ends, substantially all of said ridges being disposed to cut into the cortical bone of the diaphysis of said bone canal when said component is implanted in said bone canal.

2. The component of claim 1 wherein the component is part of a component replacement system for a joint wherein the joint is selected from the group consisting of a hip, a knee, a shoulder, an ankle, and a metacarpal joint.

3. The prosthesis component of claim 1 wherein the diaphyseal portion of the component has an overall shape which is tapered, and the ridges define the outline of the tapered portion of the prosthesis.

4. The prosthesis component of claim 1 wherein the ridges are disposed at an angle so that each ridge is parallel with or diverges no more than three degrees from a central longitudinal axis of the component from the distal to the proximal end.

5. The prosthesis component of claim 1 wherein each longitudinal ridge has at least one substantially transverse leading edge defining a step.

6. The prosthesis component of claim 5 wherein each step has an angular configuration.

7. The prosthesis component of claim 1 in which steps in the ridges define an overall tapered configuration of the component.

8. A method for implanting a tapered prosthesis component into an exposed bone canal, said canal including a diaphyseal segment, the component having a plurality of stepped longitudinal ridges disposed from a proximal to a distal end, each ridge having at least one step adapted for cutting into cortical bone, said component having at least some taper between the proximal and distal ends, the method comprising the steps of:

selecting a prosthesis component having a length and an amount of taper corresponding to a length and an amount of taper of the bone canal; and, inserting the selected component into the bone canal such that substantially all of the steps cut into cortical bone adjacent to the bone canal and thereby imbed the longitudinal ridges into the diaphyseal cortical bone.

9. The method of claim 8, wherein the step of selecting the component further includes:

selecting a component with a first number of steps for a bone canal having a first amount of taper; and, selecting a component with a greater number of steps than the first number for a bone canal having a greater amount of taper than the first amount.

10. The method of claim 8, further comprising the step of preparing the bone canal with a broach or reamer.

11. The method of claim 8, wherein the step of inserting the selected component into the bone canal includes impacting the selected component.

12. The prosthesis component for implantation into a bone canal as set forth in claim 1 wherein the ridges extend substantially from the first to the second end of the diaphyseal portion of said component.

13. The prosthesis component for implantation into a bone canal as set forth in claim 12 wherein each ridge has a plurality of bone cutting steps formed therein, substantially all of said steps being disposed to cut into the cortical bone of said bone canal when said component is implanted in said bone canal.

* * * * *